United States Patent
Church et al.

(10) Patent No.: US 12,325,865 B2
(45) Date of Patent: Jun. 10, 2025

(54) METHODS FOR INCREASING EFFICIENCY OF GENE EDITING IN CELLS

(71) Applicant: President and Fellows of Harvard College, Cambridge, MA (US)

(72) Inventors: George M. Church, Brookline, MA (US); Luhan Yang, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 886 days.

(21) Appl. No.: 16/482,294

(22) PCT Filed: Jan. 31, 2018

(86) PCT No.: PCT/US2018/016152
§ 371 (c)(1),
(2) Date: Jul. 31, 2019

(87) PCT Pub. No.: WO2018/144546
PCT Pub. Date: Aug. 9, 2018

(65) Prior Publication Data
US 2019/0352670 A1 Nov. 21, 2019

Related U.S. Application Data

(60) Provisional application No. 62/453,051, filed on Feb. 1, 2017.

(51) Int. Cl.
*C12N 9/22* (2006.01)
*C12N 15/90* (2006.01)

(52) U.S. Cl.
CPC ............ *C12N 15/907* (2013.01); *C12N 9/22* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2005/0260176 A1* 11/2005 Ayares ............... A61L 27/3604
424/93.7
2014/0011279 A1  1/2014 Yamanaka et al.
2018/0245065 A1* 8/2018 Ihry ................. C07K 14/4746

FOREIGN PATENT DOCUMENTS

WO  2018195402 A1  10/2018

OTHER PUBLICATIONS

Yang et al., Genome-wide inactivation of porcine endogenous retroviruses (PERVs). Science (2015), 350(6264): 1101-1104 and Supplemental material (Year: 2015).*
Yang et al., Genome-wide inactivation of porcine endogenous retroviruses (PERVs). Science (2015), 350(6264): 1101-1104 and Supplemental materials (Year: 2015).*
Fuks et al. Basic fibroblast growth factor protects endothelial cells against radiation-induced programmed cell death in vitro and in vivo. Cancer Research (1994), 54: 2582-2590 (Year: 1994).*
Fleischer et al., Modulating apoptosis as a target for effective therapy. Molecular Immunology (2006), 43: 1065-1079 (Year: 2006).*
Cell Lines vs. Primary Cells, Stem Cell Technologies, https://www.stemcell.com/physiological-relevance-of-human-primary-cells-vs-cell-lines [retrieved Oct. 13, 2023]). (Year: 2023).*
Shaulin et al., Induction of Mdm2 and enhancement of cell survival by bFGF. Oncogene (1997), 15: 271-2725 (Year: 1997).*
Hosokawa et al., Modulation of Mdm2 Expression and p53-Induced Apoptosis in Immortalized Human Ovarian Granulosa Cells. Endocrinology (1998), 139: 4688-4700 (Year: 1998).*
Li et al., Efficient generation of genetically distinct pigs in a single pregnancy using multiplexed single-guide RNA and carbohydrate selection. Xenotransplantation (2015), 22:20-31 (Year: 2015).*
Fedoroff, S., & Richardson, A. (1992). Colony cultures. In Protocols for Neural Cell Culture (pp. 173-183). Totowa, NJ: Humana Press. (Year: 1992).*
Richter et al., Potential of primary kidney cells for somatic cell nuclear transfer mediated transgenesis in pig. BMC Biotechnology (2012), 12:84 (Year: 2012).*
Chang et al., Disregulation of mitotic checkpoints and regulatory proteins following acute expression of SV40 large T antigen in diploid human cells. Oncogene (1997), 14: 2383-2393 (Year: 1997).*
Haimovitz-Friedman et al., Protein Kinase C Mediates Basic Fibroblast Growth Factor Protection of Endothelial Cells against Radiation-induced Apoptosis. Cancer Research, May 15, 1994, vol. 54, No. 10, pp. 2591-2597. Abstract.
Yang et al., Genome-wide inactivation of porcine endogenous retroviruses (PERVs). Science. Nov. 27, 2015, vol. 350, No. 6264, pp. 1101-1104 (Author manuscript, p. 1-6) Abstract; p. 1, col. 2, para 2.
International Search Report and Written Opinion based on PCT/US2018/016152 issued Jun. 21, 2018.
Niu et al. "Inactivation of porcine endogenous retrovirus in pigs using CRISPR-Cas9" Science; vol. 357; No. 6357; Aug. 10, 2017; pp. 1303-1307 and Supplementary Materials.

* cited by examiner

*Primary Examiner* — Abigail Vanhorn
*Assistant Examiner* — Catherine Konopka
(74) *Attorney, Agent, or Firm* — Banner & Witcoff, Ltd.

(57) ABSTRACT

The present disclosure provides methods of improving nuclease-mediated gene targeting frequencies in cells using PFTα or bFGF.

8 Claims, 2 Drawing Sheets

Specification includes a Sequence Listing.

METHODS FOR INCREASING EFFICIENCY OF GENE EDITING IN CELLS

RELATED APPLICATIONS

This application is a National Stage Application under 35 U.S.C. 371 of PCT application PCT/US2018/016152 designating the United States and filed Jan. 31, 2018; which claims the benefit of U.S. provisional application No. 62/453,051 filed on Feb. 1, 2017 each of which are hereby incorporated by reference in their entireties.

STATEMENT OF GOVERNMENT INTERESTS

This invention was made with government support under P50 HG005550-05 awarded by the National Institutes of Health (National Human Genome Research Institute). The government has certain rights in the invention.

TECHNICAL FIELD

This disclosure relates generally to gene editing.

BACKGROUND

Methods of genome editing in cells exist where the genome is cut, such as by using a nuclease, at one or more locations. Genome editing via sequence-specific nucleases is known. A nuclease-mediated double-stranded DNA (dsDNA) break in the genome can be repaired by two main mechanisms: Non-Homologous End Joining (NHEJ), which frequently results in the introduction of non-specific insertions and deletions (indels), or homology directed repair (HDR), which incorporates a homologous strand as a repair template. When a sequence-specific nuclease is delivered along with a homologous donor DNA construct containing the desired mutations, gene targeting efficiencies are increased by 1000-fold compared to just the donor construct alone.

Alternative methods have been developed to accelerate the process of genome modification by directly injecting DNA or mRNA of site-specific nucleases into a cell, such as an embryo cell, to generate a DNA double strand break (DSB) at a specified locus. DSBs induced by these site-specific nucleases can then be repaired by either error-prone non-homologous end joining (NHEJ) resulting, for example, in mutant mice and rats carrying deletions or insertions at the cut site. If a donor plasmid with homology to the ends flanking the DSB is co-injected, high-fidelity homologous recombination can produce animals with targeted integrations. Such genome editing methods include zinc finger nucleases (ZNFs) or TAL effector nucleases such as Transcription activator-like effector nucleases (TALENs).

The CRISPR type II system has been used to edit the genomes of a broad spectrum of species (see, e.g., Friedland et al., 2013; Mali et al., 2013; Hwang et al., 2013; Jiang et al., 2013; Jinek et al., 2013; Cong et al., 2013; Yin et al., 2014). CRISPR is particularly customizable because the active form consists of an invariant Cas9 protein and an easily programmable single guide RNA (sgRNA). Jinek et al., 2012. Of the various CRISPR orthologs, the *Streptococcus pyogenes* (Sp) CRISPR is the most well-characterized and widely used. The Cas9-gRNA complex first probes DNA for the protospacer-adjacent motif (PAM) sequence (-NGG for Sp Cas9), after which Watson-Crick base-pairing between the sgRNA and target DNA proceeds in a ratchet mechanism to form an R-loop. Following formation of a ternary complex of Cas9, sgRNA, and target DNA, the Cas9 protein generates two nicks in the target DNA, creating a blunt double-strand break (DSB) that is repaired by the non-homologous end joining (NHEJ) pathway or template-directed homologous recombination (HR). CRISPR methods are disclosed, for example, in U.S. Pat. Nos. 9,023,649 and 8,697,359. The development of CRISPR/Cas9 nucleases has enormously expanded our ability to engineer genetic changes in cells (Mali et al., 2013).

According to certain aspects, deaminases may be used to modify certain nucleotides as is known in the art. Deaminases are used for modifying the DNA of a cell.

Some cells, however, react negatively to genome editing resulting in DNA damage in terms of gene editing rates or survival rates. There is, therefore, a need for improved methods of engineering genetic changes in cells, such as when using CRISPR/Cas9, for example, where the genetically modified cells may generate animals, such as pigs, which can be used as potential sources of organs for transplantation.

SUMMARY

Aspects of the present disclosure are directed to the methods of increasing the efficiency of nuclease-mediated gene editing in cells. Aspects of the present disclosure are directed to a method of inhibiting apoptosis in a genetically modified cell including providing exogenous PFTα or bFGF to the cell before, during or after genetic modification of the cell. According to one aspect, the genetic modification results in breaks of a plurality of target nucleic acid sequences within the cell. According to one aspect, PFTα and bFGF are provided to the cell during genetic modification of the cell. The disclosure provides a method of inhibiting apoptosis in a genetically modified cell is provided including providing exogenous PFTα or bFGF to the cell during genetic modification of the cell, wherein the genetic modification results in breaks of a plurality of target nucleic acid sequences within the cell. According to one aspect, PFTα or bFGF are provided to the cell from within a medium in which the cell is placed. According to one aspect, the cell is genetically modified to include a nucleic acid sequence that encodes a nuclease, which when expressed cuts a target nucleic acid sequence. According to one aspect, the nuclease is a Cas nuclease, a Cas nickase, a nuclease null Cas bound to a nuclease, a zinc finger nuclease, a meganuclease or a TALEN. According to one aspect, the cell is a prokaryotic cell or a eukaryotic cell. According to one aspect, the cell is a stem cell, an embryonic stem cell, a pluripotent stem cell, a zygote, or a germ line cell. According to one aspect, the cell is a somatic cell or a primary cell. According to one aspect, the cell is an animal cell. According to one aspect, the cell is a porcine cell. According to one aspect, the plurality of target nucleic acid sequences comprises a porcine endogenous retrovirus (PERV) gene. According to one aspect, the PERV gene comprises apol gene. According to one aspect, one or more copies of the pol gene are inactivated. According to one aspect, all copies of the pol gene in the cell are inactivated.

Aspects of the present disclosure provide an engineered or genetically modified cell including an exogenous nucleic acid sequence encoding a programmable nuclease, which when expressed cuts a target nucleic acid sequence, and exogenous PFTα or bFGF. According to one aspect, the nuclease is a Cas nuclease, a Cas nickase, a nuclease null Cas bound to a nuclease, a zinc finger nuclease, a meganuclease or a TALEN. According to one aspect, the cell is a prokaryotic cell or a eukaryotic cell. According to one aspect, the cell is a stem cell, an embryonic stem cell, a pluripotent stem cell, a zygote, or a germ line cell. According to one aspect, the cell is a somatic cell or a primary cell. According to one aspect, the cell is an animal cell. According to one aspect, the cell is a porcine cell. According to one aspect, the plurality of target nucleic acid sequences comprises a porcine endogenous retrovirus (PERV) gene. According to one aspect, the PERV gene comprises a pol gene. According to one aspect, one or more copies of the pol gene are inactivated. According to one aspect, all copies of the pol gene in the cell are inactivated.

DETAILED DESCRIPTION

Figure 1:
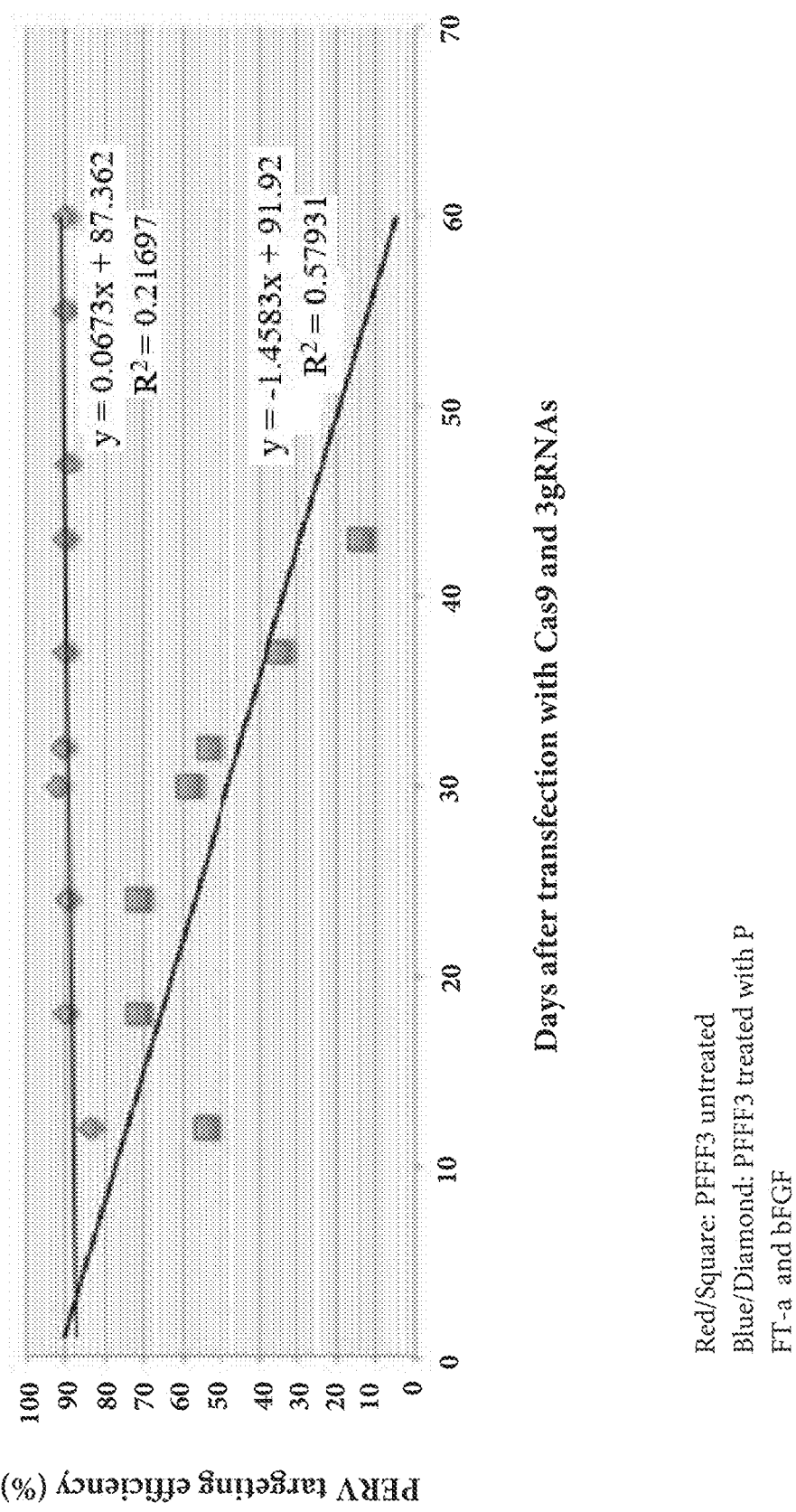
FIG. 1 is a graph of data showing that treatment with PFTα and bFGF prevents senescence and allows isolation of 100% PERV-free clonal cell lines.

The present disclosure provides methods to limit, reduce, inhibit, or eliminate a negative effect, such as toxicity, associated with genome editing in cells, such as primary cells, where DNA damage can lead to the negative effect. For example, nuclease-based genome editing, such as with a CRISPR/Cas system, can result in toxicity that severely limits gene editing in target cells. This present disclosure provides methods of limiting, reducing, inhibiting, or eliminating this toxicity and improving gene targeting frequencies in target cells by using small molecule p53 inhibitors, such as PFTa, (pifithrin a) and bFGF (basic fibroblast growth factor). See Grandela et al. (2007). p53 is required for etoposide-induced apoptosis of human embryonic stem cells. Stem Cell Research 1, 116-128 and Qin et al. (2007). Regulation of Apoptosis and Differentiation by p53 in Human Embryonic Stem Cells. Journal of Biological Chemistry 282, 5842-5852 each of which are hereby incorporated by reference in its entirety.

According to one aspect, porcine endogenous retroviral (PERV) elements are genetically modified within porcine cells for the purpose of generating porcine cell lines and animals that lack active PERVs and are useful resources for xenotransplantation therapies. Inactivating PERVs allows xenotransplantation to be a strategy to provide organs for human transplantation insofar as immunological incompatibility is reduced that may otherwise result from cross-species transmission of porcine endogenous viruses (PERVs). PERVs infect, propagate, and evolve in human primary cells over time. The present disclosure provides methods of large scale genome editing, such as in primary cells, to inactivate all PERVs, such as in a primary porcine fibroblast cell line, to prevent PERV transmission to human cells, and wherein the genetically modified cells are treated with PFTα or bFGF to improve or increase gene editing rates or cell survival rates compared to genome edited cells which have not been treated with PFTα or bFGF.

In particular, the present disclosure involves methods of genetic engineering used to inactivate PERVs, such as in primary porcine cell lines. Such cells are treated with PFTα and bFGF so as to limit, reduce, inhibit, or eliminate negative effects of such genome modification. The invention further includes porcine cell lines and tissues, embryos, and animals generated from these treated cells, that lack active PERVs and are thus suitable resources for xenotransplantation. It is to be understood that aspects of the present disclosure are not limited to any particular genome modification. Instead, genome modification of porcine endogenous retroviral (PERV) elements in porcine cells, such as primary porcine cells, is exemplary with the use of PFTα and bFGF. The present disclosure is directed to methods of increasing gene targeting frequencies by treating a cell with PFTα or bFGF, wherein the cell is genetically modified to include a gene editing system or is otherwise genetically modified.

The genetically modified cell comprises an expression construct encoding a programmable DNA nuclease or a meganuclease. The cells are contacted with a small molecule p53 inhibitor such as PFTα or bFGF. A "programmable DNA nuclease" as used herein means a DNA nuclease that can be engineered to recognize and cleave a desired sequence in the genome of the cell. Examples of a programmable DNA nuclease include a class 2 clustered regularly-interspaced short palindromic repeat (CRISPR) nucleases, a zinc finger nuclease (ZFN), and a Transcription Activator-Like Effector nuclease (TALEN). Each of these types of programmable DNA nucleases is well known in the art.

Described herein is the use of the Clustered Regularly Interspaced Short Palindromic Repeats (CRISPR) and CRISPR associated (Cas) proteins (CRISPR/Cas) system to achieve highly efficient and simultaneous targeting of multiple nucleic acid sequences in cells. Particular examples of a CRISPR nuclease include a CRISPR associated protein 9 (Cas9) nuclease, a CRISPR from *Prevotella* and *Francisella* 1 nuclease (Cpf1), a Class 2 candidate 1 nuclease (C2c1), a Class 2 candidate 2 nuclease (C2c2), and a Class 2 candidate 3 nuclease (C2c3). "Cas9 nucleases" exist in many bacteria, including *S. pyogenes, S. thermophilus, S. aureus*, and *Neisseria meningitidis*. A "Cas9 nuclease" includes a Cas9 nuclease with native (or wild-type) nuclease activity, as well as modified versions of a Cas9 nuclease, such as SpCas9-HF1 ("high fidelity variant number 1;" Kleinstiver et al., 2016), eSpCas9 ("enhanced specificity Cas9;" Slaymaker et al., 2016), Cas9 nickases (e.g., Cong et al., 2013; Mali et al., 2013) and nuclease-deficient or nuclease-null Cas9 (e.g., Jinek et al., 2012) fused to a nuclease domain (e.g., FokI). Examples of meganucleases include I-SceI meganuclease and I-CreI meganuclease, as well as engineered derivatives thereof (e.g., Thermes et al., 2002; Arnould et al., 2011).

Aspects of the present disclosure are directed to the modification of genomic DNA, such as multiplex modification of DNA, in a cell (e.g., primary cell, stem cell, somatic cell, germ line cell, zygote) using one or more guide RNAs (ribonucleic acids) to direct an enzyme having nuclease activity expressed by the cell, such as a DNA binding protein having nuclease activity, to a target location on the DNA (deoxyribonucleic acid) wherein the enzyme cuts the DNA and an exogenous donor nucleic acid is inserted into the DNA, such as by homologous recombination. According to one aspect, the DNA is genomic DNA, mitochondrial DNA, viral DNA, or exogenous DNA. Aspects of the present disclosure include cycling or repeating steps of DNA modification in a cell to create a cell having multiple modifications of DNA within the cell. Modifications can include insertion of exogenous donor nucleic acids. Modifications can include deletion of endogenous nucleic acids.

Multiple nucleic acid sequences can be modulated (e.g., inactivated) by a single step of introducing into a cell, which expresses an enzyme, and nucleic acids encoding a plurality of RNAs, such as by co-transformation, wherein the RNAs are expressed and wherein each RNA in the plurality guides the enzyme to a particular site of the DNA, the enzyme cuts the DNA. According to this aspect, many alterations or modification of the DNA in the cell are created in a single cycle.

According to one aspect, the cell expressing the enzyme has been genetically altered to express the enzyme such as by introducing into the cell a nucleic acid encoding the enzyme and which can be expressed by the cell. In this manner, aspects of the present disclosure include cycling the steps of introducing RNA into a cell which expresses the enzyme, introducing exogenous donor nucleic acid into the cell, expressing the RNA, forming a co-localization complex of the RNA, the enzyme and the DNA, and enzymatic cutting of the DNA by the enzyme. Insertion of a donor nucleic acid into the DNA is also provided herein. Cycling or repeating of the above steps results in multiplexed genetic modification of a cell at multiple loci, i.e., a cell having multiple genetic modifications.

According to certain aspects, DNA binding proteins or enzymes within the scope of the present disclosure include a protein that forms a complex with the guide RNA and with the guide RNA guiding the complex to a double stranded DNA sequence wherein the complex binds to the DNA sequence. According to one aspect, the enzyme can be an RNA guided DNA binding protein, such as an RNA guided DNA binding protein of a Type II CRISPR System that binds to the DNA and is guided by RNA. According to one aspect, the RNA guided DNA binding protein is a Cas protein, such as a Cas9 protein. This aspect of the present disclosure may be referred to as co-localization of the RNA and DNA binding protein to or with the double stranded DNA. In this manner, a DNA binding protein-guide RNA complex may be used to cut multiple sites of the double stranded DNA so as to create a cell with multiple genetic modifications, such as disruption of one or more (e.g., all) copies of a gene.

According to certain aspects, a method of making multiple alterations to target DNA in a cell expressing an enzyme that forms a co-localization complex with RNA complementary to the target DNA and that cleaves the target DNA in a site specific manner is provided including (a) introducing into the cell a first foreign nucleic acid encoding one or more RNAs complementary to the target DNA and which guide the enzyme to the target DNA, wherein the one or more RNAs and the enzyme are members of a co-localization complex for the target DNA, wherein the one or more RNAs and the enzyme co-localize to the target DNA, the enzyme cleaves the target DNA to produce altered DNA in the cell, and repeating step (a) multiple times to produce multiple alterations to the DNA in the cell.

In some aspects, a method of inactivating expression of one or more target nucleic acid sequences in a cell comprises introducing into a cell one or more ribonucleic acid (RNA) sequences that comprise a portion that is complementary to all or a portion of each of the one or more target nucleic acid sequences, and a nucleic acid sequence that encodes a Cas protein; and maintaining the cells under conditions in which the Cas protein is expressed and the Cas protein binds and inactivates the one or more target nucleic acid sequences in the cell.

In other aspects, a method of modulating one or more target nucleic acid sequences in a cell comprises introducing into the cell a nucleic acid sequence encoding an RNA complementary to all or a portion of a target nucleic acid sequence in the cell; introducing into the cell a nucleic acid sequence encoding an enzyme that interacts with the RNA and cleaves the target nucleic acid sequence in a site specific manner; and maintaining the cell under conditions in which the RNA binds to complementary target nucleic acid sequence forming a complex, and wherein the enzyme binds to a binding site on the complex and modulates the one or more target nucleic acid sequences.

In the methods described herein, the introducing step can comprise transfecting the cell with the one or more RNA sequences and the nucleic acid sequence that encodes the Cas protein. In some embodiments, the one or more RNA sequences, the nucleic acid sequence that encodes the Cas protein, or a combination thereof are introduced into a genome of the cell. In some embodiments, the expression of the Cas protein is induced.

Materials and methods of genome editing having utility in methods described herein include Certo et al. (2012). Coupling endonucleases with DNA end-processing enzymes to drive gene disruption. Nature Methods 9, 973-975; Chavez et al. (2015). Highly efficient Cas9-mediated transcriptional programming. Nature Methods 12, 326-328; Chen et al. (2011). High-frequency genome editing using ssDNA oligonucleotides with zinc-finger nucleases. Nature Methods 8, 753-755; Chu et al. (2015). Increasing the efficiency of homology-directed repair for CRISPR-Cas9-induced precise gene editing in mammalian cells. Nature Biotechnology 33, 543-548; Cong et al., "Multiplex genome engineering using CRISPR/Cas systems," Science, 2013, 339(6121): p. 819-23; Fu et al. (2014). Improving CRISPR-Cas nuclease specificity using truncated guide RNAs. Nature Biotechnology 32, 279-284; Jinek et al., "A programmable dual-RNA-guided DNA endonuclease in adaptive bacterial immunity," Science, 2012. 337(6096): p. 816-21; Jinek et al., "RNA-programmed genome editing in human cells," elife, 2013. 2: p. e00471; Mali et al. (2013). RNA-guided human genome engineering via Cas9. Science 339, 823-826; Mali et al., "CAS9 transcriptional activators for target specificity screening and paired nickases for cooperative genome engineering," Nature Biotechnology 31, 833-838 (2013); Maruyama et al. (2015). Increasing the efficiency of precise genome editing with CRISPR-Cas9 by inhibition of nonhomologous end joining. Nature Biotechnology 33, 538-542.

In the methods described, eukaryotic cells or prokaryotic cells are envisioned as being useful in the methods described herein. According to one aspect, the cell is a primary cell. According to one aspect, the cell is from an embryo. The cell can be a stem cell, zygote, or a germ line cell. In embodiments where the cell is a stem cell, the stem cell is an embryonic stem cell or pluripotent stem cell. In other embodiments, the cell is a somatic cell. In embodiments, where the cell is a somatic cell, the somatic cell is a eukaryotic cell or prokaryotic cell. The eukaryotic cell can be an animal cell, such as from a pig, mouse, rat, rabbit, dog, horse, cow, non-human primate, human.

The stem cell to be genetically modified can be an embryonic stem cell (ESC) or a somatic stem cell such as hiPSC, a hematopoietic stem cell, a neural stem cell, or a mesenchymal stem cell. In some variations, the genetically modified stem cell is human. In other variations, the stem cell is that of a non-human mammal, such as a non-human primate, a mouse, a pig or a rat. Methods of obtaining and growing various types of stem cells are well known the in the art (e.g., Takahashi et al., 2007; Yu et al., 2007; Robinton & Daley, 2012; Drawnel et al., 2014; Li et al., 2015; US 2012/0087933; US 2014/0377865; US 2015/0299712; US 2015/0307841; US 2016/0032250; US 2016/0060594).

The one or more target nucleic acid sequences can comprise a porcine endogenous retrovirus (PERV) gene. For example, the PERV gene can comprise a pol gene. The methods described herein can inactivate, modulate, or effect one or more copies of the pol gene. In some embodiments, all copies of the pol gene in the cell are inactivated.

In some embodiments, the genetically modified cell also comprises an RNA sequence such as an sgRNA (single guide RNA) complementary to a target nucleic acid sequence of the cell genome. The genetically modified cell may comprise multiple such sgRNAs, each complementary to a different target nucleic acid sequence of the cell genome. In some variations in which the programmable DNA nuclease is a CRISPR nuclease, the expression construct encoding the CRISPR nuclease also includes a nucleic acid encoding one or more sgRNAs. In other variations, one or more sgRNAs can be provided using one or more separate expression constructs. Types of sgRNAs are well known in the art (e.g., US 2014/0356959; US 2015/0259704).

The one or more RNA sequences can be about 10 to about 1000 nucleotides. For example, the one or more RNA sequences can be about 15 to about 200 nucleotides. According to one aspect, the one or more RNAs is a guide RNA. According to one aspect, the one or more RNAs is a tracrRNA-crRNA fusion.

In some aspects an engineered cell comprises one or more endogenous viral genes; and one or more exogenous nucleic acid sequences that comprise a portion that is complementary to all or a portion of one or more target nucleic acid sequences of the one or more endogenous viral genes; wherein each of the one or more endogenous viral genes of the cell are modulated.

In another aspect, an engineered cell can comprise a plurality of endogenous retroviral genes; and one or more exogenous nucleic acid sequences that comprise a portion that is complementary to all or a portion of one or more target nucleic acid sequences of the plurality of endogenous viral genes; wherein each of the plurality of endogenous viral genes of the cell are modulated.

The engineered cells described herein can comprise a porcine endogenous retrovirus (PERV) gene. For example, the PERV gene can comprise apol gene. In some aspects, modulation of the pol gene inactivates one or more copies of the pol gene. For example, all or substantially all copies of the pol gene in the cell are inactivated.

Methods of delivering exogenous nucleic acids to cells are well known in the art and include plasmid vectors, viral vectors (e.g., lenti-, adeno-, and adeno-associated viral vectors), and ribonucleoproteins. Plasmid donors with >1 kb homology arms for small changes (1-100 bp) are particularly useful. See Shui et al., 2016. Nucleic acids can also be delivered by electroporation, injection, or lipofection. The nucleic acid encoding the programmable DNA nuclease or meganuclease can be provided in separate expression constructs or the same expression construct.

The following examples are intended to illustrate but not limit this disclosure.

Example I

Inactivation of PERVs in an Immortalized Porcine Cell Line

All 62 copies of active PERVs in an immortalized porcine cell line (PK-15) were inactivated using CRISPR-Cas9 genome-editing technology as described in Yang, L. et al. Genome-wide inactivation of porcine endogenous retroviruses (PERVs). *Science* 350, 1101-1104 (2015) hereby incorporated by reference in its entirety. Materials and methods useful in the present disclosure are described in or can be derived from Yang, L. et al. Genome-wide inactivation of porcine endogenous retroviruses (PERVs). *Science* 350, 1101-1104 (2015).

Example II

Inactivation of PERVs in Primary Porcine Cells

A primary porcine female fetal fibroblast (PFFF3) cell line was obtained. This primary cell line can be cloned via SCNT to produce porcine embryos bearing the same genotype as the PFFF3 somatic cell. All PERVs in PFFF3 were inactivated using multiplex modification. The PERV-free clonal PFFF3 cell lines were isolated and viable embryos were cloned from the isolated cells. The embryos are implanted in sows to mature PERV-free pigs.

To map and characterize the functional PERVs present in the PFFF3 cell line, the genome of PFFF3 was sequenced and assembled with whole-genome sequencing and Dovetail assembly. Using qPCR, we identified copies of PERV A, copies of PERV B, and no copies of PERV C. Copies of subtype A and of B contained the intact reverse transcriptase (pol) gene. These results were validated with ddPCR. To target these PERVs for inactivation, three CRISPR guide RNAs (gRNAs) specific to the catalytic core of PERV pol were designed. The first gRNA was designed to target one strand of the DNA, the second and third gRNAs, the other strand. The second and the third gRNAs were identical except for the nucleotide two bases before the PAM sequence. The region of PERV pol targeted by the second gRNAs in PFFF3 contained an allele that was not apparent in the consensus sequence. Therefore, a third gRNA was designed to target this minor allele. The sequences of the three sgRNAs used to target a conserved region of PERV pol in PFFF3 are as follows:

```
PERV sgRNA 1
ggtaccctcctccagtacgtgg

PERV sgRNA2
ggtcatccacgtactggaggagg

PERV sgRNA3
ggtcatccacgtactggatgagg.
```

Stable expression of Cas9 and the three sgRNAs was achieved by integrating a piggyBac transposon carrying these elements into the PFFF3 genome. The PFFF3 cell line was established expressing a Piggybac-Cas9/3gRNAs construct. Cas9 and 2 gRNAs were carried in the same vector. Cas9 expression was induced by addition of doxycycline.

After treatment with CRISPR-Cas9 and the three gRNAs for twelve days, it was observed that in the population of PFFF3 cells, 37% of the PERV pol loci had acquired inactivating mutations. The PFFF3 population displayed 37% targeting efficiency of the PERV pol locus by Cas9. The targeting efficiency in single cell clones derived from the 37% PERV-free population exhibited a bimodal distribution wherein clones had low editing efficiencies while other clones had high editing efficiencies. In some clones, 100% of the PERVs had been targeted and mutated. This bimodal distribution resembled results achieved in Yang, L. et al. Genome-wide inactivation of porcine endogenous retroviruses (PERVs). *Science* 350, 1101-1104 (2015). According to the present disclosure, 100% PERV-free PFFF3 cell lines were unable to be isolated. The targeting efficiency of the PFFF3 population decreased over time in culture.

Example III

Treating PERV-Free PFFF3 Cells with as PFTα or bFGF

Figure 2:
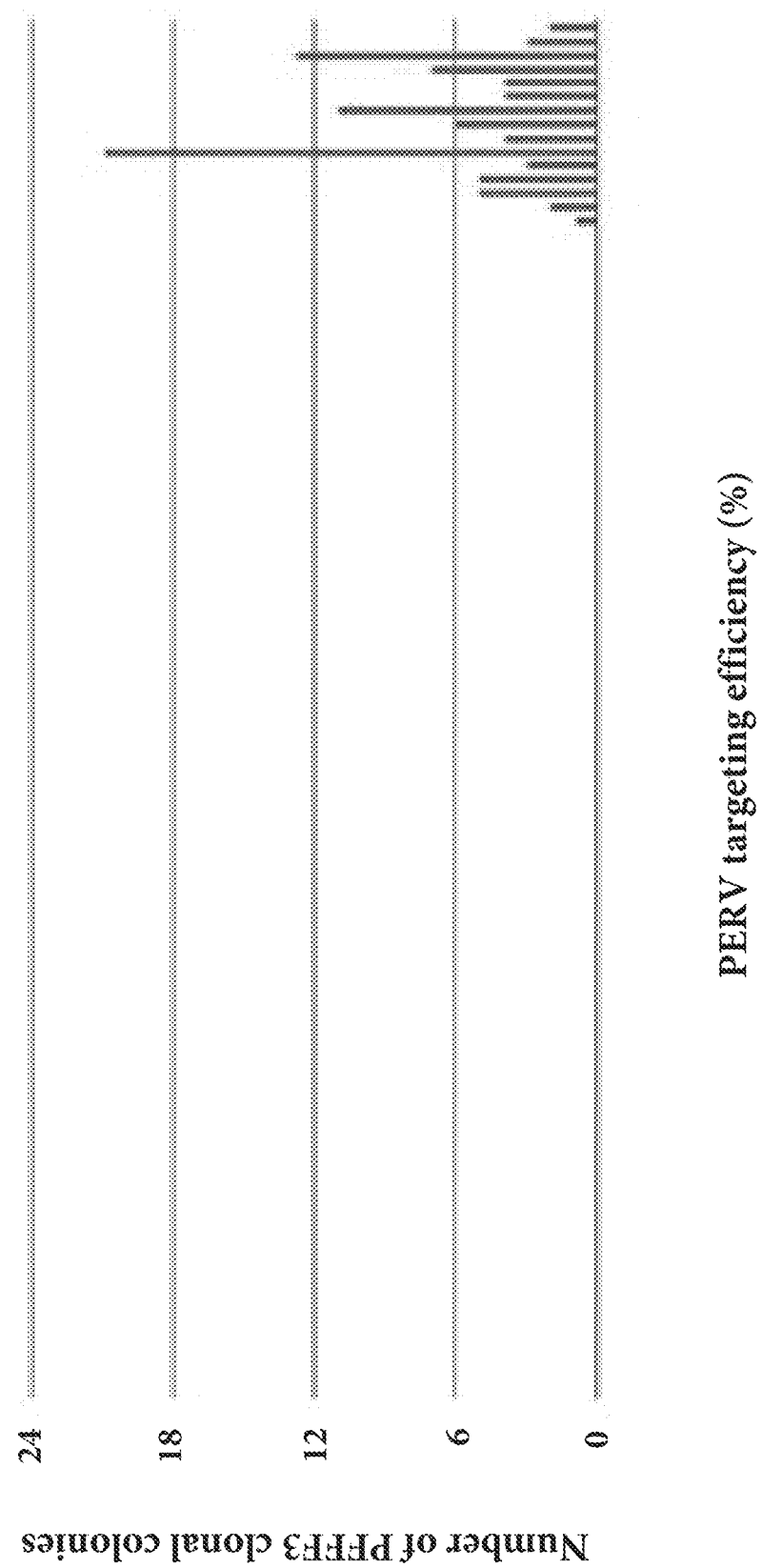
FIG. 2 is a graph of data showing PERV targeting efficiency in individual expanded clones from a population of PFFF3 treated with PFTα and bFGF during genetic modification.

Without wishing to be bound by scientific theory, 100% PERV-free PFFF3 clones did not expand to colonies because the primary cells were sensitive to DNA damage resulting from simultaneous DNA cleavage by Cas9 and a resultant abundance of DNA double-strand breaks and became senescent or apoptotic under the conditions of stress caused by Cas9-induced DNA cleavage. Methods described herein where cells are treated with PFTα and/or bFGF mitigate the stress from multiplex DNA damage and support clonal expansion of 100% PERV-free cells. Such DNA damage decreases targeting efficiency of the PFFF3 population over time and results in the inability to obtain 100% PERV-free PFFF3 clonal cell lines. Methods described herein are directed to inhibiting senescence and/or apoptosis pathways with small-molecule drugs so as to increase the targeting efficiency of the PFFF3 population and enhance viability of the highly edited clones. Treatment of the genomically modified PFFF3 cells described herein with the combination of PFTα and bFGF during genetic modification prevented senescence and allowed isolation of 100% PERV-free clonal cell lines. (See FIG. 1). Treatment of the genomically modified PFFF3 cells described herein with the combination of PFTα and bFGF during genetic modification increased the average targeting efficiency of the resulting PFFF3 population. (See FIG. 2). Treatment with SV40 large T antigen also resulted in increased average targeting efficiency. The distribution of the targeting efficiencies of single cell clones treated with PFTα and bFGF was approximately bimodal, and 100% PERV-free PFFF3 clonal cell lines were isolated. The eradication of pol activity was validated by RNA-seq with confirmation that all pol transcripts had been mutated.

Example IV

Off Target Effects

The 100% PERV-free PFFF3 cell line was tested for off-target effects of CRISPR-Cas9. Karyotype analysis of 100% PERV-free PFFF3 indicated normal chromosomal structure. RNAseq analysis showed that the transcription profile of 100% PERV-free PFFF3 closely resembled that of WT PFFF3. Additionally, off-target mutations were not observed in the transcripts of 100% PERV-free PFFF3. CRISPR-Cas9 had not introduced detectable off-target damage in the 100% PERV-free PFFF3. Genome-wide inactivation of PERVs had not altered global gene expression profiles.

Example V

Eliminating In Vitro Transmission of PERVs from PFFF3 Cells to Human Cells

The genome-wide disruption of PERV pol as described herein eliminated in vitro transmission of PERVs from PFFF3 to human cells. No reverse transcriptase (RT) activity in the cell culture supernatant of the 100% PERV-free PFFF3 was detected, indicating that these cells produced few or no PERV particles. WT and 100% PERV-free PFFF3 cells were co-cultured with HEK293 cells for 7 days. PERV pol, gag, and env sequences were detected in the HEK293 cells that had been cultured with WT PFFF3, indicating transmission of PERVs to the human cells. However, in HEK293 co-cultured with 100% PERV-free PFFF3, the presence of pol, gag, or env sequences was not observed above background levels, indicating that the inactivation of all PERVs in PFFF3 had eliminated transmission to human cells. From the combination of DNA and RNA genotype analysis as well as expression and infectivity analysis, the activity of PERV pol was eradicated, whose reverse transcription is essential for PERV proliferation and infection, thereby eliminating the risk of PERV transmission to human cells. Embryos from the 100% PERV-free PFFF3 may be cloned to generate a PERV-free pig, such as using the methods described in Vajta G., Lewis I. M., Hyttel P., Handm G. A., Trounson A. O. Somatic cell cloning without micromanipulators. *Cloning* 3:89-95 (2001) hereby incorporated by reference in its entirety.

The invention claimed is:

1. A method of making a population of PERV-free porcine cells, the method comprising:
 (a) genetically modifying a primary porcine cell which comprises porcine endogenous retrovirus (PERV) genes by providing a vector comprising a nucleic acid sequence which encodes a nuclease and three sgRNAs to the primary porcine cell, wherein the nuclease is expressed and cuts the PERV genes, thereby producing a genetically modified, PERV-free, primary porcine cell,
 (b) providing an exogenous pifithrin α (PFTα) and a basic fibroblast growth factor (bFGF) to the primary porcine cell concomitant with step (a),
 (c) contacting the primary porcine cell with a large SV40 T antigen to increase targeting efficiency,
 (d) isolating the genetically modified, PERV-free primary porcine cell, and expanding the genetically modified, PERV-free porcine cell to a population of PERV-free porcine cells, wherein the population of PERV-free porcine cells exhibits a lack of PERV transmission as evidenced by co-culturing a cell with the population of PERV-free porcine cells.

2. The method of claim 1, wherein the nuclease is a Cas nuclease, a Cas nickase, or a nuclease null Cas bound to a nuclease.

3. The method of claim 2, wherein the nuclease is the Cas nuclease.

4. The method of claim 3, wherein the Cas nuclease is Cas9.

5. The method of claim 1, wherein the PERV genes comprise PERV pol genes.

6. The method of claim 1, wherein of the PFTα and the bFGF inhibit apoptosis in the primary porcine cell.

7. The method of claim 1, wherein the PFTα and the bFGF increase gene editing rates in the primary porcine cell.

8. The method of claim 1, wherein the PFTα and the bFGF increase a cell survival rate in the primary porcine cell.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtaccctcc tccagtacgt gg                                            22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 2
ggtcatccac gtactggagg agg                                               23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtcatccac gtactggatg agg                                               23
```